United States Patent [19]

Inoue et al.

[11] 4,049,740
[45] Sept. 20, 1977

[54] METHOD FOR ACTIVATION OF ALUMINUM CHLORIDE COMPLEX ALKYLATION CATALYST

[75] Inventors: Yasuhiko Inoue; Keizo Uyeo, both of Niihama, Japan

[73] Assignee: Sumitomo Chemical Company, Ltd., Osaka, Japan

[21] Appl. No.: 619,253

[22] Filed: Oct. 3, 1975

Related U.S. Application Data

[63] Continuation of Ser. No. 399,744, Sept. 21, 1973, abandoned.

[30] Foreign Application Priority Data

Sept. 21, 1972 Japan .................... 47-95522

[51] Int. Cl.$^2$ .................... C07C 3/56; C07C 3/52; B01J 27/32
[52] U.S. Cl. .................... 260/671 R; 208/13; 252/414; 260/671 B
[58] Field of Search ............ 252/414, 415, 411, 442; 208/13; 260/671 R, 671 B

[56] References Cited

U.S. PATENT DOCUMENTS

| 1,202,081 | 10/1916 | McAfee | 208/13 |
| 2,338,711 | 1/1944 | D'Ouville et al. | 260/671 R |
| 2,394,412 | 2/1946 | Veltman | 252/414 |
| 2,488,190 | 11/1949 | Hepp | 260/671 R |
| 3,478,118 | 11/1969 | Sorgenti | 260/671 B |
| 3,600,296 | 7/1971 | Rieve | 208/13 |
| 3,657,148 | 4/1972 | Becker et al. | 260/671 B |
| 3,846,334 | 11/1974 | Di Fiore et al. | 252/414 |

*Primary Examiner*—Winston A. Douglas
*Assistant Examiner*—P. E. Konopka
*Attorney, Agent, or Firm*—Birch, Stewart, Kolasch and Birch

[57] ABSTRACT

A method for activation of an aluminum chloride complex used as a catalyst in the nuclear alkylation of an aromatic compound with an alkyl halide or an olefin which comprises washing a part of or all of the aluminum chloride complex with a paraffinic hydrocarbon.

7 Claims, No Drawings

METHOD FOR ACTIVATION OF ALUMINUM CHLORIDE COMPLEX ALKYLATION CATALYST

This application is a continuation of application Ser. No. 399,744, filed on Sept. 21, 1973, now abandoned.

The present invention relates to a method for activation of an alkylation catalyst. More particularly, it relates to a method for activation of an aluminum chloride complex used on a catalyst in the nuclear alkylation of an aromatic compound with an alkyl halide or an olefin.

It is well known that anhydrous aluminum chloride is used as a catalyst in the nuclear alkylation of aromatic compounds, i.e. the alkylation of an aromatic compound on the aromatic ring, with an alkyl halide or an olefin. In this case, aluminum chloride is, even if used in a solid form, present in a liquid state in the reaction system and forms a complex which is called "red oil", "slurry", "contact oil" or the like. This complex is supposed to mainly consist of aluminum chloride and poly-membered aromatic compounds, or of polysubstituted aromatic compounds and hydrogen chloride, but its details are not yet clarified (cf. H. C. Brown et al.: Industrial and Engineering Chemistry, 45, 1462-1469 (1953)).

Such aluminum chloride complex is a highly valuable catalyst, which is employed in various fields of industry. However, it is the drawback of this catalyst that its catalytic activity is rapidly lowered with its use.

For activation of the aluminum chloride complex of which the catalytic activity is decreased, there has been proposed a method wherein the complex in a liquid state is heated so as to evaporate off organic compounds such as benzene dissolved therein [German Pat. No. 858,242]. Since, however, the complex in a liquid state has an extremely high viscosity, a troublesome operation for a long period of time is required. In addition, the effect of activation attained by such operation is not satisfactory from the industrial viewpoint.

As the result of an extensive study, it has been found that washing of an aluminum chloride complex used as a catalyst in the nuclear alkylation of an aromatic compound with a paraffinic hydrocarbon can eliminate substances lowering the catalytic activity contained therein to make the aluminum chloride complex activated. The present invention is based on this finding.

According to the present invention, there is provided a method for activation of an aluminum chloride complex used in the nuclear alkylation of an aromatic compound with an alkyl halide or an olefin which comprises washing a part of or all of the aluminum chloride complex with a paraffinic hydrocarbon.

The aluminum chloride complex to be activated by this invention is the one which results from aluminum chloride which has been used one or more times as a catalyst in the nuclear alkylation of an aromatic compound with an alkyl halide or an olefin, having a lowered catalytic activity in comparison with that of the starting fresh aluminum chloride and containing aluminum chloride as its essential constituent.

As the paraffinic employed for washing in the method of the present invention, there may be employed any paraffinic hydrocarbon which is liquid under the washing conditions. Usually, a paraffinic hydrocarbon which is liquid at room temperature under an ordinary pressure is employed. Specific examples of the paraffinic hydrocarbon are pentane, hexane, heptane, octane, nonane decane, undecane, dodecane, tridecane, tetradecane, pentadecane, heptadecane, octadecane, nonadecane, eicosane, etc. In general, paraffinic hydrocarbons having 5 to 24 carbon atoms are favorably employed. They may be used alone or in admixture. Also, they may contain one or more aromatic hydrocarbons in an amount of not more than 20% by weight.

The paraffinic hydrcarbon may be used in an amount sufficient for washing of the aluminum chloride complex, i.e. for good separation of the mixture into two layers comprising the aluminum chloride complex and the paraffinic hydrocarbon. Usually, 0.1 part by volume or more, preferably 0.2 to 50 parts by volume, of the paraffinic hydrocarbon is employed to 1 part by volume of the aluminum chloride complex. When the amount of the paraffinic hydrocarbon is smaller than 0.1 part by volume, the activation effect becomes much lowered. On the other hand, the use of a larger amount of the paraffinic hydrocarbon does not afford any particular influence on the activation effect, and the upper limit of the amount used may be determined from an economical viewpoint.

The activation of the aluminum chloride complex can be achieved simply by washing the same with the paraffinic hydrocarbon, but it is particularly advantageous to wash or dilute the aluminum chloride complex with an aromatic hydrocarbon prior to the washing with the paraffinic hydrocarbon, because, by contacting with an aromatic hydrocarbon, substances decreasing the catalytic activity which are contaminated in the aluminum chloride complex are apt to be removed into the aromatic hydrocarbon. Examples of the aromatic hydrocarbon are benzene, toluene, xylene, ethylbenzene, diethylbenzene, dodecylbenzene, etc. These may be used alone or in admixture.

The temperature during the washing of the aluminum chloride complex with the praffinic hydrocarbon is not particularly limited. At too low of a temperature, however, the viscosity of the aluminum chloride complex is increased so that the operation becomes difficult. At too high of a temperature, there may be caused undesirable side reactions such as isomerization and decomposition of the paraffinic hydrocarbon. Usually, a temperature between 10° and 100° C is favorable.

The activation may be performed in various manners, of which some examples are as follows: admixing the aluminum chloride complex with the paraffinic hydrocarbon in a vessel and separating them after allowing the mixture to stand for a while; effecting the operations batchwise or continuously using a mixing vessel and a separation vessel which are provided separately from each other; contacting the aluminum chloride complex with the paraffinic hydrocarbon in a counter current multistage extraction apparatus and separating them after allowing the mixture to stand for a while; contacting them in a counter current extraction apparatus of the column type such as the packed column type, plate column type or spray column type and separating them after allowing the mixture to stand for a while, etc.

The paraffinic hydrocarbon recovered after washing of the aluminum chloride complex contains substances which decrease the catalytic activity thereof. It can be purified, for example, by distillation and then may be reused for the washing.

The catalytic activity of the aluminum chloride complex after the washing is greatly increased. In some cases, the aluminum chloride complex to be activated may be admixed with aluminum chloride or with metallic aluminum and hydrogen chloride prior to the washing. The activated aluminum chloride complex may be used itself or in an admixture with aluminum chloride, hydrogen chloride or metallic aluminum and hydrogen chloride as the alkylation catalyst.

The activation of the aluminum chloride complex may be effected each time after the alkylation reaction or after performing the alkylation reactions two or more times.

In the alkylation reaction, there may be used any aromatic compound which is susceptible to alkylation. Examples of such aromatic compound are benzene, toluene, xylene, phenol, naphthalene, biphenyl, etc. Examples of the utilizable alkyl halide include an alkyl chloride, an alkyl bromide, an alkyl fluoride and an alkyl iodide, of which the alkyl moiety may be cyclic or non-cyclic alkyl and have 1 to 20 carbon atoms (e.g. methyl, ethyl, propyl, butyl, pentyl, hexyl, heptyl, octyl, nonyl, decyl, undecyl, dodecyl, tetradecyl, hexadecyl, octadecyl, cyclopentyl, cyclohexyl). Examples of the utilizable olefin are cyclic or non-cyclic olefins having 2 to 20 carbon atoms such as ethylene, propylene, butene, isobutene, pentene, hexene, heptene, octene, nonene, decene, undecene, dodecene, tetradecene, octadecene, cyclopentene, cyclohexene and cycloheptene.

The amount of the aluminum chloride complex to be used in the alkylation reaction is varied depending on the kind of the starting compound, the purpose and the like. Usually, the use of an equimolar amount or less of the catalyst with respect to the alkylating agent, i.e. the alkyl halide or the olefin, is preferable.

The temperature of the alkylation reaction is usually in a range of 0° to 100° C, though it may vary depending on the purpose.

The alkylation reaction may be effected batchwise or continuously or semi-continuously by any conventional procedure. For assuring a sufficient contact area of the organic layer with the catalyst layer, it is desirable to stir the reaction system vigorously and efficiently.

After completion of the alkylation reaction, the reaction mixture may be allowed to stand for a while, whereby two layers, i.e. the upper layer containing the alkylation product and the unreacted starting compound and the lower layer containing the aluminum chloride complex, are separated. The lower layer is collected and subjected to the activation method as mentioned above.

By adoption of the activation method of the invention, the amount of the catalyst to be used in the alkylation can be decreased so that the expense is saved and only a small vessel is needed for storage.

Practical and presently preferred embodiments of the invention are illustratively shown in the following Examples.

EXAMPLE 1

In a 10 liter volume glass lined reactor which is equipped with a stirrer, a thermometer and a reflux condenser serving also as an outlet for gas and whose atmosphere is replaced by nitrogen, there are charged anhydrous aluminum chloride (50 g), benzene (3liters) as a material to be alkylated and a mixture of n-decane, n-undecane, and n-dodecane in a ratio of 2 : 5 : 3 by volume (4 liters) as a diluent, and the temperature is elevated up to 85° C. Lauryl chloride (500 ml) as an alkylating agent is added thereto, and the alkylation reaction is effected for 15 minutes. The reaction mixture is allowed to stand until the reddish brown, viscous aluminum chloride complex precipitates at the bottom of the reactor. Then, the supernatant is separated off, and the aluminum chloride complex (117 ml) is recovered.

The thus recovered aluminum chloride complex and n-decane (100 ml) are charged in a 300 ml volume flask, and the mixture is stirred at 75° C for 30 minutes under a nitrogen stream. The mixture is allowed to stand for a while, and the precipitate at the bottom of the flask is collected to obtain an activated aluminum chloride complex (104 ml).

In the same glass-lined reactor as mentioned above, there are charged benzene (3 liters) as a material to be alkylated, a mixture of n-decane, n-undecane and n-dodecane in a ratio of 2 : 5 : 3 by volume (4 liters) as a diluent and the above obtained activated aluminum chloride complex, and the temperature is elevated up to 85° C. Lauryl chloride (500 ml) as an alkylating agent is added thereto, and the alkylation reaction is effected for 15 minutes.

The above procedure comprising the alkylation reaction and the washing of the aluminum chloride complex is repeated six times, and the conversion resulting from the alkylation reaction is calculated from the consumption of lauryl chloride at the end of the second, the fourth and the sixth times.

The results are shown in Table 1.

Table 1

| | Second time | Fourth time | Sixth time |
|---|---|---|---|
| Conversion (%) | 100 | 85 | 62 |

EXAMPLE 2

The alkylation reaction is effected as in Example 1, and the reaction mixture is allowed to stand until the reddish brown, viscous aluminum chloride complex precipitates at the bottom of the reactor. The supernatant is separated off, and the aluminum chloride complex (120 ml) is recovered.

The thus recovered aluminum chloride complex and hexane (110 ml) are charged in a 300 ml volume flask, and the mixture is stirred at 30° C for 30 minutes under a nitrogen stream. The mixture is allowed to stand for a while, and the precipitate at the bottom of the flask is collected to obtain an activated aluminum chloride complex (107 ml).

Using the above obtained activated aluminum chloride complex, the procedure comprising the alkylation reaction and the washing of the aluminum chloride complex is repeated six times, and the conversion of the alkylation reaction is calculated.

The results are shown in Table 2.

Table 2

| | Second time | Fourth time | Sixth time |
|---|---|---|---|
| Conversion (%) | 100 | 80 | 58 |

EXAMPLE 3

The alkylation reaction is effected as in Example 1, and the reaction mixture is allowed to stand until the reddish brown, viscous aluminum chloride complex precipitates at the bottom of the reactor. The supernatant is separated off, and the aluminum chloride complex (118 ml) is recovered.

The thus recovered aluminum chloride complex and benzene (100 ml) are charged in a 300 ml volume flask, and the mixture is stirred at 75° C for 30 minutes under a nitrogen stream. The mixture is allowed to stand for a while, and the precipitated aluminum chloride complex is collected. The thus collected aluminum chloride complex is further washed with n-dodecane (100 ml) at 75° C for 10 minutes in a 300 ml volume flask. After the mixture is allowed to stand for a while, the precipitate at the bottom of the flask is collected to obtain an activated aluminum chloride complex (110 ml).

Using the thus obtained activated aluminum chloride complex, the procedure comprising the alkylation reaction and the washing of the aluminum chloride complex is repeated six times, and the conversion of the alkylation reaction is calculated.

The results are shown in Table 3.

Table 3

|  | Second time | Fourth time | Sixth time |
| --- | --- | --- | --- |
| Conversion (%) | 100 | 86 | 65 |

Reference Example 1

As in Example 1 but using aluminum chloride complex repeatedly without washing, the alkylation reaction is repeated six times, and the conversion of the alkylation reaction is calculated.

The results are shown in Table 4.

Table 4

|  | Second time | Fourth time | Sixth time |
| --- | --- | --- | --- |
| Conversion (%) | 96 | 65 | 34 |

Comparing the above results with those in Examples 1 to 3, it is understood that the activation according to the invention is extremely advantageous.

EXAMPLE 4

In the same glass lined reactor as in Example 1 whose atmosphere is replaced by nitrogen, there are charged anhydrous aluminum chloride (50 g), benzene (7 liters) as a material to be alkylated and n-heptane (500 ml), and a small amount of hydrogen chloride gas as a promotor is introduced therein at 30° C. Dodecene-1 (1500 ml) as an alkylating agent is added thereto, and the alkylation reaction is effected for 10 minutes. The reaction mixture is allowed to stand until the reddish brown, viscous aluminum chloride complex precipitates at the bottom of the reactor. The supernatant is separated off, and the aluminum chloride complex (121 ml) is recovered.

The thus recovered aluminum chloride complex and benzene (100 ml) are charged in a 500 ml volume flask, and the mixture is stirred at 70° C for 30 minutes under a nitrogen stream. The mixture is allowed to stand for a while, and the precipitated aluminum chloride complex is collected. The thus collected aluminum chloride complex is further washed with n-dodecane (150 ml) at 75° C for 30 minutes in a 500 ml volume flask. After the mixture is allowed to stand for a while, the precipitate at the bottom of the flask is collected to obtain an activated aluminum chloride complex (118 ml).

In the same glass lined reactor as above, there are charged benzene (7 liters) as a material to be alkylated, n-heptane (500 ml) and the above obtained activated aluminum chloride complex, and dodecene-1 (1500 ml) as an alkylating agent is added thereto at 30° C. The alkylation reaction is effected for 10 minutes.

The above procedure comprising the alkylation reaction and the washing of the aluminum chloride complex is repeated six times, and the conversion of the alkylation reaction is calculated after the second, the fourth and the sixth times.

The results are shown in Table 5.

Table 5

|  | Second time | Fourth time | Sixth time |
| --- | --- | --- | --- |
| Conversion (%) | 100 | 98 | 70 |

Reference Example 2

As in Example 4 but using aluminum chloride complex repeatedly without washing, the alkylation reaction is repeated six times, and the conversion of the alkylation reaction is calculated.

The results are shown in Table 6.

Table 6

|  | Second time | Fourth time | Sixth time |
| --- | --- | --- | --- |
| Conversion (%) | 95 | 70 | 47 |

Comparing the above results with those in Example 4, it is understood that the activation according to the invention is extremely advantageous.

EXAMPLE 5

The aluminum chloride complex obtained after the sixth alkylation reaction in Example 1 is washed with n-decane, and a part (20 g) of the washed product is admixed with anhydrous aluminum chloride (1.0 g) to give a complex catalyst.

The thus obtained complex catalyst is charged in a 1 liter volume glass reactor which is equipped with a stirrer, a thermometer and a reflux condenser serving also as an outlet for gas and whose atmosphere is replaced by nitrogen, and benzene (300 ml) and a mixture of n-decane, n-undecane and n-dodecane in a ratio of 2 : 5 : 3 by volume (400 ml) are added thereto. The temperature is elevated up to 85° C, and lauryl chloride (50 ml) is added thereto while stirring. The alkylation reaction is effected for 15 minutes. The conversion of the alkylation reaction is 95%.

Reference Example 3

A part (20 g) of the aluminum chloride complex obtained after the sixth alkylation reaction in Reference Example 1 is admixed with anhydrous aluminum chloride (1.0 g) to give a complex catalyst. Using the thus obtained complex catalyst, the alkylation reaction is effected as in Example 5. The conversion is 87%.

What is claimed is:

1. In a method for the nuclear alkylation of an aromatic hydrocarbon compound in which said aromatic hydrocarbon compound is reacted with an alkyl halide in the presence of a catalytic amount of an aluminum chloride-aromatic hydrocarbon compound complex under reaction conditions which cause nuclear substitution in said aromatic hydrocarbon compound by an alkyl radical to be effected, the improvement which comprises:

A. Separating the aluminum chloride-aromatic hydrocarbon compound complex from the reaction mixture resulting from said nuclear alkylation of an aromatic hydrocarbon compound, and B. Regenerating said aluminum chloride-aromatic hydrocarbon compound complex by washing at least part of it with a straight chain paraffinic hydrocarbon of 5–24 carbon atoms which is liquid under the washing conditions and in an amount of at least 0.1 part by volume of said paraffinic hydrocarbon per 1 part by volume of aluminum chloride-aromatic hydrocarbon complex to permit the subsequent formation of two separate layers, the lower layer consisting solely of the regenerated aluminum chloride-aromatic hydrocarbon compound complex, said washing being conducted in a temperature range in which isomerization of said paraffinic hydrocarbon will not be effected, separating said lower layer of regenerated aluminum chloride-aromatic hydrocarbon complex and recycling said regenerated catalyst to said alkylation reaction.

2. The method of claim 1, wherein the washing of the separated aluminum chloride-aromatic hydrocarbon compound complex is effected at a temperature in the range of 10° to 100° C.

3. The method of claim 1, wherein the amount of catalyst employed is equimolar with respect to the alkyl halide alkylating agent.

4. The method of claim 1, wherein said paraffinic hydrocarbon is used in a mixture with at least one aromatic hydrocarbon in an amount of not more than 20% by weight based on the weight of the mixture.

5. The method of claim 1, wherein the separated aluminum chloride-aromatic hydrocarbon compound complex is washed with an aromatic hydrocarbon selected from the group consisting of benzene, toluene, xylene, ethyl benzene and diethyl benzene and is separated therefrom prior to the washing with said paraffinic hydrocarbon.

6. The method of claim 1, wherein the nuclear alkylation of the aromatic hydrocarbon is effected in the temperature range of 0° to 100° C.

7. The method of claim 1, wherein the nuclear alkylation reaction is effected in the presence of a liquid paraffinic hydrocarbon diluent.

* * * * *